United States Patent
Jun et al.

(10) Patent No.: US 7,861,575 B2
(45) Date of Patent: Jan. 4, 2011

(54) MICRO GAS SENSOR AND MANUFACTURING METHOD THEREOF

(75) Inventors: Chi Hoon Jun, Daejeon (KR); Sang Choon Ko, Daejeon (KR); Moon Youn Jung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 266 days.

(21) Appl. No.: 12/142,695

(22) Filed: Jun. 19, 2008

(65) Prior Publication Data

US 2009/0151429 A1 Jun. 18, 2009

(30) Foreign Application Priority Data

Dec. 17, 2007 (KR) ............... 10-2007-0131984

(51) Int. Cl.
*G01N 7/00* (2006.01)
*G01N 27/12* (2006.01)

(52) U.S. Cl. .............. 73/31.06; 73/25.01; 73/25.05

(58) Field of Classification Search ........ 73/23.2–31.06
See application file for complete search history.

(56) References Cited

U.S. PATENT DOCUMENTS 4,580,439 A * 4/1986 Manaka ................. 73/31.06

| | | | |
|---|---|---|---|
| 5,019,885 A | 5/1991 | Yagawara et al. | |
| 5,759,493 A * | 6/1998 | Raisanen ................. | 422/88 |
| 5,902,556 A * | 5/1999 | Van De Vyver et al. ..... | 422/174 |
| 6,161,421 A | 12/2000 | Fang et al. | |
| 6,202,467 B1 * | 3/2001 | Iovdalsky et al. ............ | 73/23.2 |
| 6,906,392 B2 * | 6/2005 | Benzel et al. ............... | 257/414 |
| 7,276,745 B2 | 10/2007 | Nakagawa et al. | |
| 2005/0199041 A1 * | 9/2005 | Weber et al. .............. | 73/31.06 |
| 2007/0062812 A1 * | 3/2007 | Weber et al. ............... | 204/431 |
| 2008/0134753 A1 * | 6/2008 | Jun et al. .................... | 73/23.2 |
| 2008/0233752 A1 * | 9/2008 | Ko et al. .................... | 438/700 |

FOREIGN PATENT DOCUMENTS

JP 2007-132762 A 5/2007
KR 10-2006-0094664 A 8/2006

* cited by examiner

*Primary Examiner*—Lisa M Caputo
*Assistant Examiner*—Punam Roy

(57) ABSTRACT

A micro gas sensor is disclosed including a substrate; an open cavity formed in the substrate; an electrode pad separation groove formed on the substrate; a first and a second electrode pads formed over the substrate and electrically insulated from each other by the electrode pad separation groove; a micro heater connected to the first electrode pad and configured of a bridge structure suspended over the open cavity; a first sensing electrode extending from the first electrode pad and suspended over the open cavity; a second sensing electrode extending from the first electrode pad and suspended over the open cavity; and a gas sensing film electrically coupled to the micro heater and filling a gap between the first and the second sensing electrodes.

25 Claims, 12 Drawing Sheets

MICRO GAS SENSOR AND MANUFACTURING METHOD THEREOF

CROSS-REFERENCE TO RELATED APPLICATIONS

This application claims the priority of Korean Patent Application No. 10-2007-0131984 filed on Dec. 17, 2007, in the Korean Intellectual Property Office, the disclosure of which is incorporated herein by reference.

BACKGROUND OF THE INVENTION

1. Field of the Invention

The present invention relates to a micro gas sensor and a method of manufacturing the same for precisely measuring a gas concentration, and more particularly, to a micro gas sensor and a method of manufacturing the same that has low power consumption, a rapid heating and cooling time, high durability, high sensitivity characteristics, a capability of easily forming a gas sensing film by using various materials, and a plurality of suspended sensing electrodes, which can be miniaturized and mass-produced at low cost through a simple manufacturing process using only a single pattern mask.

This work was supported by the IT R&D program of MIC/IITA [2006-S-007-02, Ubiquitous Health Monitoring Module and System Development].

2. Description of the Related Art

As concerns for the environment grow, the development of a micro sensor capable of obtaining precise and various information within a short time is required. Particularly, efforts to achieve miniaturization, high precision, and low cost of a gas sensor used for easily measuring a concentration of a gas have been continued to implement comfortableness of living spaces, cope with a bad industrial environment, and manage food manufacturing processes, etc.

Recently, a conventional gas sensor that has a ceramic sintering or thick film structure has been gradually developed to be a micro gas sensor having a microelectromechanical system (MEMS) type applying semiconductor manufacturing technologies.

In terms of measuring methods, in a method that has been widely used for the current gas sensor, when a gas is absorbed into a gas sensing film of a sensor, changes in electrical characteristics of the gas sensing film are measured. In this method, a metal oxide such as a tin oxide $SnO_2$ is used as the gas sensing film, and changes in electrical conductivity due to a concentration of the gas are measured. This means the method is simple. Here, the metal oxide gas sensing film shows significant changes in measured values when the gas sensing film is heated at a high temperature and operated. Therefore, in order to rapidly and accurately measure the gas concentration, accurate temperature control is necessary. In addition, before the measurement, gas or moistures absorbed into the gas sensing film are compulsively removed by heating at a high temperature to recovery the gas sensing film to an initial state, and the gas concentration is measured. Therefore, temperature characteristics of the gas sensor directly affect main measurement factors such as measurement sensitivity, a recovery time, a response time, and the like of the sensor.

Therefore, for effective heating, a micro heater that can uniformly heat a local portion of the gas sensing film may be used. However, if a power consumed to control the temperature for measurement using the micro gas sensor is high, a large battery or power supply is needed although volumes of the sensor and a measurement circuit are small, and this causes an increase in a size of the entire measurement system. Therefore, in order to implement the micro gas sensor, a structure consuming low power has to be considered first.

Conventionally, in order to manufacture the micro gas sensor, a silicon substrate having a very high thermal conductivity is mainly used. Therefore, in order to reduce heat loss, etched pits or grooves are formed in a sensor structure by using a bulk micromachining process, a suspended structure separated from the substrate is formed, and a micro heater, an insulating layer, and a gas sensing film are sequentially formed on the structure, thereby reducing parts of the heat loss. However, in this case, wet etching using a crystallization direction of the substrate itself is used in the manufacturing processes, so that miniaturization of the sensor device is limited, and there is a problem in that properties of an etching reagent such as a potassium hydroxide (KOH) are not compatible with standard complementary metal-oxide semiconductor (CMOS) manufacturing processes.

In terms of commercialization, the micro gas sensor has to operate for two or three years stably. Considering that the gas sensor is repeatedly heated or cooled by the micro heater at a temperature ranging from 150° C. to 500° C., that is a very strict condition. Here, failures may occur due to mechanical impacts and thermal stress caused by a temperature gradient applied to the sensor structure suspended from the substrate. Therefore, in preparation for the failures, in a conventional method, a basal supporting layer of the suspended structure is formed by a single layer including a silicon dioxide $SiO_2$ layer or a silicon nitride $Si_3N_4$ layer, stacked layers, or multilayers thereof to be $Si_3N_4/SiO_2$, $SiO_2/Si_3N_4$, $Si_3N_4/SiO_2/Si_3N_4$, or $SiO_2/Si_3N_4/SiO_2$ to implement stress balance. Thereafter, the micro heater, the sensing electrode, and the gas sensing film are sequentially patterned to solve vulnerability in the structure. However, although the stress balance is implemented, the aforementioned insulating materials are fragile and have low thermal conductivity. Therefore, if lacks of temperature uniformity increase in the heated suspended structure, structural safety cannot be guaranteed. Therefore, durability of the micro gas sensor device is related to materials of the structure and design of the micro heater.

In addition, to form functional elements including a thermal insulation structure for the conventional micro gas sensor device, by using five or six, or ten or more pattern masks, on a substrate, thin film deposition, photoresist coating, micro-patterning, thin film etching are repeatedly performed to sequentially stack and manufacture the functional elements in a vertical direction. Therefore, there are problems in that manufacturing cost consumed for the semiconductor manufacturing processes are increased, it takes a long time, and a yield is decreased.

Recently, for a gas sensing film having a core role in the micro gas sensor, materials including metal oxide, metal, semiconductors, polymer, nano-materials, and the like have been studied. A conventional gas sensing film is formed by directly micro-patterning sensing film materials on a surface of the sensor device by using a lift-off process using a pattern mask, or formed by moving the sensor device mounted to a micro stage to a lower portion of a micropipette to be micro-aligned, titrating materials, and performing post-treatment thereon. However, the aforementioned methods have a problem in that a unique micro-patterning process according to materials to be used for the gas sensing film has to be developed. Particularly, when the nano-materials are used, the problem is worsened. In addition, in a case where a high-cost precise mechanical micro-alignment apparatus is needed, additional manufacturing cost and time are consumed. Therefore, a technique for easily forming a micro pattern on a particular position of a surface of the micro gas sensor device so that various types of material can be used for the gas sensing film is needed.

SUMMARY OF THE INVENTION

Hereinafter, representative techniques conventionally used for a micro gas sensor using micromachining are described.

U.S. patent application Ser. No. 11/358,621 discloses a structure of a typical micro gas sensor in which anisotropic wet etching is performed on a rear surface of a silicon substrate by bulk micromachining to a predetermined thickness to form a cavity and an insulating layer membrane, and a micro heater, a pair of electrodes, and a gas sensing film are formed thereon. The performed silicon wet etching in the manufacturing processes is simple, however, there are problems in that a depth and a shape of the cavity cannot be precisely controlled and since a device die is relatively large, manufacturing cost is high. In addition, a supporting layer has a suspended structure using only the insulating layer, so that the micro gas sensor is vulnerable to repeated thermal or mechanical impacts.

U.S. Pat. No. 6,161,421 discloses an aluminum oxide ($Al_2O_3$) insulating layer, finger electrodes, and a gas sensing film formed on a SiC-based suspended structure by performing wet etching on a rear surface of a silicon substrate to a predetermined thickness. Particularly, although the SiC heater is used to improve temperature characteristics, the SiC is formed by performing a special deposition process using high temperature, so that there is a problem of compatibility with a standard semiconductor manufacturing process.

U.S. Pat. No. 5,019,885 discloses a structure in which grooves are formed on a front surface of a silicon substrate by bulk micromachining using an etching reagent, and a plurality of pairs of electrodes heated by a plurality of micro heaters at a predetermined temperature are connected to a plurality of gas sensing films on a plurality of suspended structures across the grooves. The structure has problems in that since the wet etching is used, a depth or a shape of the groove cannot be controlled and durability is low.

The aforementioned conventional micro gas sensor still needs to improve upon in terms of power consumption, temperature characteristics, durability, micro-patterning of gas sensing layers, measurement sensitivity, sizes, manufacturing cost, and the like.

Therefore, the present invention provides a micro gas sensor which has low power consumption, durability against mechanical or thermal impacts, includes a gas sensing film that is formed by using various types of material such as metal oxide, metal, semiconductors, polymer, nano-materials, and the like and has a rapid heating and cooling time, has an improved output corresponding to changes in a gas concentration, that is, an improved sensitivity, and can be mass-produced at low cost.

According to an aspect of the present invention, there is provided a micro gas sensor including: a substrate; an open cavity and electrode pad separation grooves formed on the substrate; a plurality of electrode pads formed on an upper portion of the substrate and electrically insulated from each other by the electrode pad separation grooves; a micro heater connected to a plurality of the electrode pads by a bridge structure and suspended on the open cavity; a plurality of sensing electrodes formed on the same plane between the micro heater and a plurality of the electrode pads in a cantilever array and suspended on the open cavity; and a gas sensing film formed to be hung down between microelectrode finger spacings of a plurality of the sensing electrodes to represent changes in characteristics according to a gas concentration by contacting surfaces of the micro heater and a plurality of the sensing electrodes.

In the above aspect of the present invention, the micro gas sensor may further include die separation lines for separating devices which are simultaneously formed along with the open cavity and the electrode pad separation grooves on the substrate from each other.

In addition, the substrate may be made of a material selected from the group consisting of semiconductors, conductors, and insulators.

In addition, the electrode pad separation groove may have a shape of X so that the gas sensing film is not contacted to the lower portion of the substrate and is hung down between edge portions of a plurality of the electrode pads.

In addition, the micro heater, a plurality of the sensing electrodes, and a plurality of the electrode pads may be disposed on the same plane and formed by a structure in which an insulating layer and a conductive layer are stacked on the substrate.

In addition, the insulating layer may have a function of electrically insulating the substrate, the micro heater, a plurality of the sensing electrodes, and a plurality of the electrode pads from each other and include one or more of a silicon oxide ($SiO_2$) layer and a silicon nitride ($Si_3N_4$) layer, or a modified silicon oxide layer including a borophosphosilicate glass (BPSG) layer, a phosphosilicate glass (PSG) layer, or a spin-on-glass (SOG) layer.

In addition, the conductive layer may be made of one or more of metal and a material including metal, and the insulating layer and the conductive layer may have a stacked structure to serve as a supporting layer having a high thermal conductivity and durability.

In addition, a plurality of the electrode pads may be connected to both end portions of the micro heater and one end portions of a plurality of the sensing electrodes so as to be electrically connected to external electrical wires.

In addition, a plurality of the sensing electrodes may include a center sensing electrode, a left sensing electrode, and a right sensing electrode which have a suspended structure for sensing changes in electrical characteristics according to reaction of the gas sensing film.

In addition, the center sensing electrode, the left sensing electrode, and the right sensing electrode may include a plurality of microelectrode fingers formed as one or more suspended cantilevers.

In addition, the center sensing electrode may be connected to the micro heater and has a structure in a shape of a comb or a fish bone.

In addition, one end portions of the left sensing electrode and the right sensing electrode may face the center sensing electrode to form a pair of IDEs (interdigitated electrodes) that are electrically insulated from each other, and the other end portions may be connected to a plurality of the electrode pads so as to be connected to external electrical wires.

In addition, the left sensing electrode and the right sensing electrode may be electrically connected to a plurality of the electrode pads to form a single sensing electrode.

In addition, the gas sensing film may be buried or hung down between microelectrode finger spacings of a plurality of the sensing electrodes composed of the center sensing electrode, the left sensing electrode, and the right sensing electrode.

In addition, the gas sensing film may be formed one of materials including metal oxide, metal, semiconductors, polymer, and nano-materials or a combination thereof.

According to another aspect of the present invention, there is provided a method of manufacturing a micro gas sensor including: forming an insulating layer on a substrate; coating a photoresist on the insulating layer and performing patterning on the insulating layer to form electrode pad separation grooves and die separation lines by using one pattern mask; forming a silicon trench structure from a surface of an exposed substrate to a predetermined depth by performing anisotropic etching on the exposed substrate in a vertical direction by using the patterned insulating layer as an etching masking layer; simultaneously forming an open cavity, the electrode pad separation grooves, the die separation lines, a micro heater pattern including an insulating layer suspended on the open cavity, and a plurality of sensing electrode patterns by performing isotropic etching on the substrate having the silicon trench structure; simultaneously forming a micro heater, a plurality of sensing electrodes, and a plurality of electrode pads on the same plane by depositing a conductive layer on the insulating layer; and forming a gas sensing film so that the gas sensing film is not contacted to a lower portion of the substrate by capillary force and surface tension and is contacted to surfaces of the micro heater and a plurality of the sensing electrodes by dropping a liquid precursor between microelectrode finger spacings formed by a plurality of the sensing electrodes.

In the above aspect of the present invention, method may further include separating dies formed on the substrate by using the die separation lines from each other and performing packaging thereon.

In addition, forming the silicon trench structure may be performed by anisotropic dry etching on the substrate by using reactive ion etching (RIE) or deep-RIE using plasma or charged ion particles.

In addition, in forming the micro heater pattern and a plurality of the sensing electrode patterns, isotropic dry etching may be additionally performed on the substrate having the silicon trench structure to suspend an insulating layer pattern by using plasma etching or gas phase etching.

In addition, the micro heater may have a bridge structure which has both side surfaces at which a plurality of comb-shaped fingers are formed and be formed at the center upper portion of the open cavity, and a plurality of the sensing electrodes may be patterned so that each of left and right sides of the bridge has a plurality of cantilever arrays and an end portion of each cantilever is connected to a plurality of the electrode pads.

In addition, a plurality of the sensing electrodes may include a center sensing electrode corresponding to the comb-shaped fingers connected to the micro heater, a left sensing electrode corresponding to the left cantilever arrays, and a right sensing electrode corresponding to the right cantilever arrays.

In addition, in forming the gas sensing film, a liquid precursor formed by one of materials including metal oxide, metal, semiconductors, polymer, and nano-materials or a combination thereof may be used.

In addition, in forming the gas sensing film, the gas sensing film may be formed to be buried or hung down between microelectrode finger spacings of a plurality of the sensing electrodes by using surface tension and capillary force of the liquid precursor.

In addition, in forming the gas sensing film, one of micro dropping, e-beam evaporation, sputtering, pulsed laser deposition, sol-gel, chemical vapor deposition (CVD), spray coating, dip coating, and screen printing may be used.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
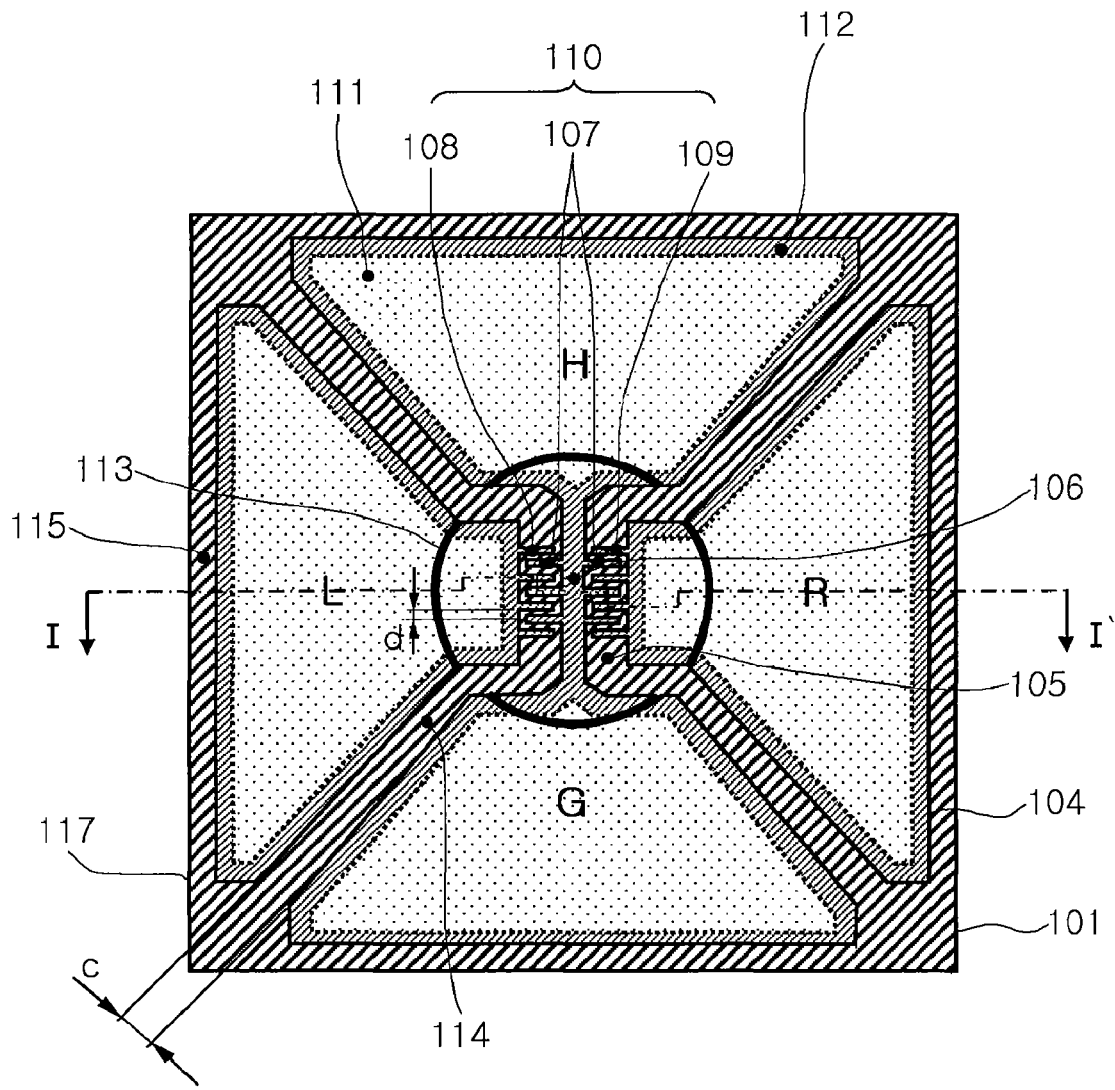
FIG. 1 is a top plan view illustrating a micro gas sensor having four electrode pads according to an embodiment of the present invention.

Exemplary embodiments of the present invention will now be described in detail with reference to the accompanying drawings.

In the description, the detailed descriptions of well-known functions and structures may be omitted so as not to hinder the understanding of the present invention.

In the drawings, lengths and sizes of layers and regions may be exaggerated for clarity. In addition, it will be understood that when an element or layer is referred to as being "on" another element or layer, the element or layer can be directly on another element or layer or intervening elements or layers.

Like reference numerals designate like elements throughout the specification.

FIG. 1 is a top plan view illustrating a micro gas sensor having four electrode pads according to an embodiment of the present invention. FIG. 3 is a cross-sectional view illustrating the micro gas sensor taken along line I-I' of FIG. 1. The cross-sectional view of FIG. 3 is the same as a cross-sectional view illustrating a micro gas sensor taken along line I-I' of FIG. 2.

Referring to FIGS. 1 and 3, the micro gas sensor according to the present invention includes a silicon substrate 101, an open cavity 105 formed on the substrate 101 to a predetermined depth in order to minimize heat loss, an electrode pad separation groove 114 formed on the substrate 101 to a predetermined depth to enable electrical insulation, a die separation line 115 formed on the substrate 101 to a predetermined depth to easily separate sensor devices from each other, an anchor 111 formed on the substrate 101 to fix a suspended structure, an insulating layer (denoted by 102 in FIG. 3) for electrically insulating a structure formed to be suspended on an upper portion of the open cavity 105 from the substrate 101, a supporting layer 104 having a conductive layer 103 stacked on the insulating layer 102 to have high thermal conductivity and high durability, a micro heater 106 which is formed by using the conductive layer 103 on the insulating layer 102 and has a bridge structure suspended on the open cavity 105 to emit heat, center sensing electrodes 107 which are formed by using the conductive layer 103 on the insulating layer 102 and attached to both sides of the micro heater 106 to function as heat spreaders and include one or more microelectrode fingers 110 having a cantilever structure, a left sensing electrode 108 and a right sensing electrode 109 each of which has an end that is a counterpart to the center sensing electrode 107 to form a pair of interdigitated electrodes (IDEs) and the other end fixed to the substrate 101 by the anchor 111 through the insulating layer 102 to be suspended on the open cavity 105, four electrode pads 112 which are formed by using the conductive layer 103 on the insulating layer 102 and connected to both end portions of the micro heater 106 and one end portions of the sensing electrodes 107, 108, and 109 to be electrically connected to external electrical wires, and a gas sensing film 113 which is made of a material selected from the group consisting of metal oxide, metal, semiconductors, polymer, and nano-materials to be connected with surfaces of the micro heater 106, the center sensing electrode 107, the left sensing electrode 108, and the right sensing electrode 109 suspended on the center portion of the open cavity 105.

Figure 2:
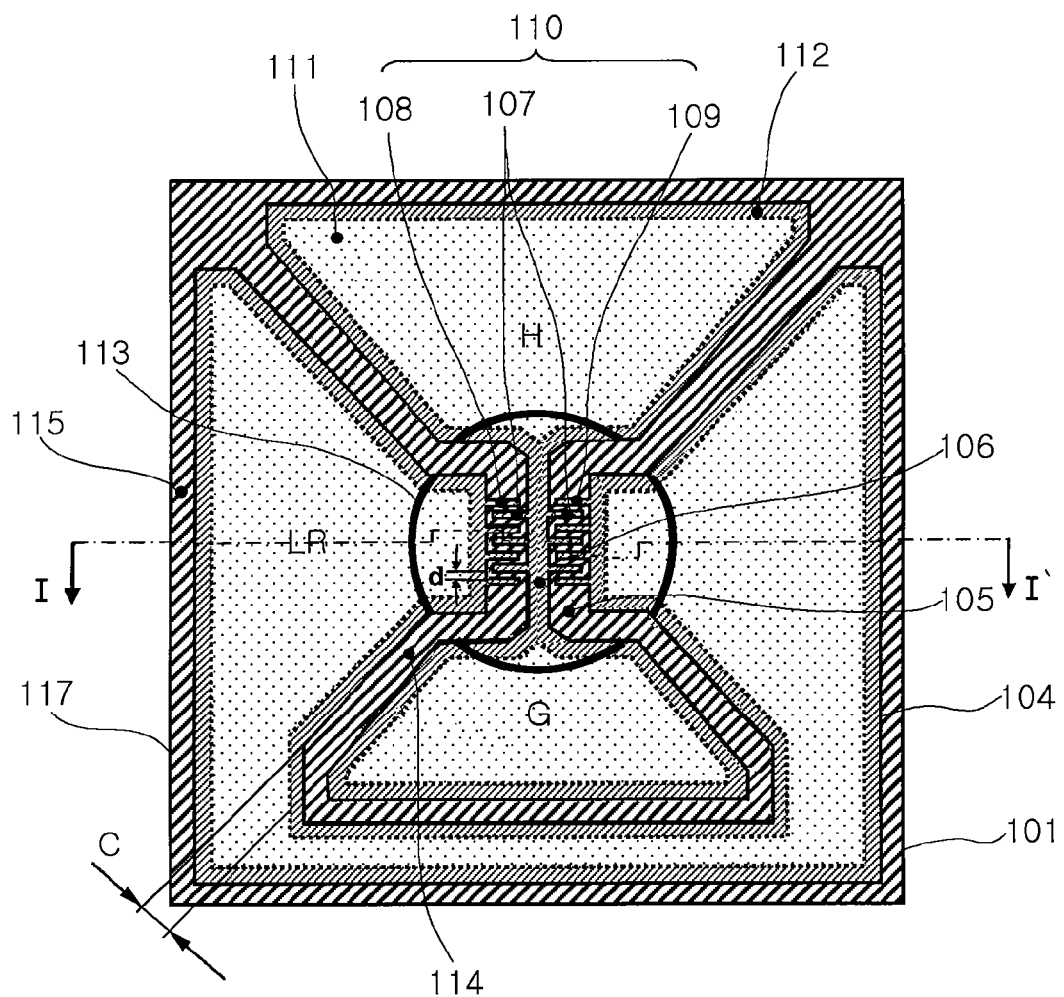
FIG. 2 is a top plan view illustrating a micro gas sensor having three electrode pads according to another embodiment of the present invention.
Figure 3:
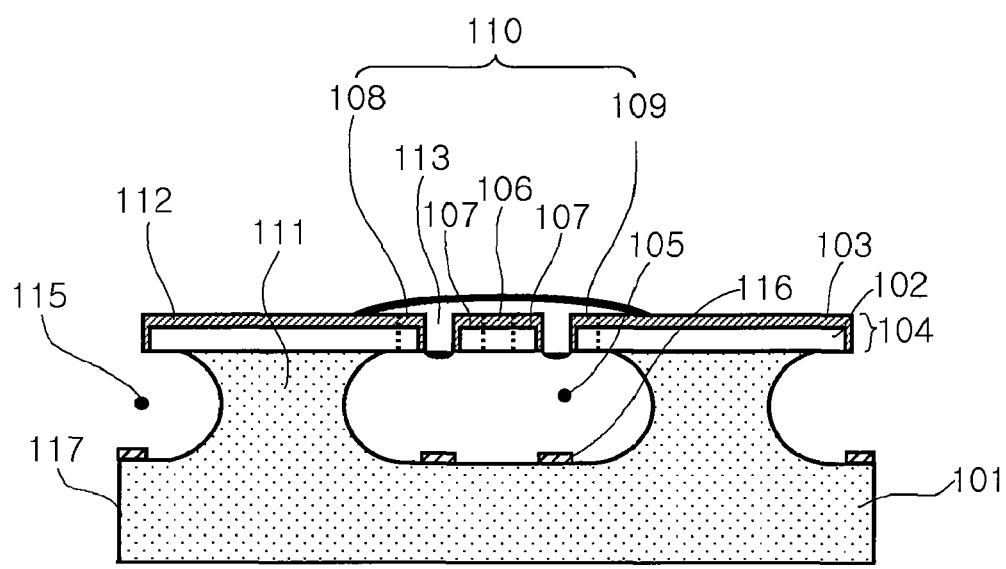
FIG. 3 is a cross-sectional view illustrating the micro gas sensors of FIGS. 1 and 2 taken along line I-I'.

FIG. 2 is a top plan view illustrating a micro gas sensor having three electrode pads according to another embodiment of the present invention.

Comparing to FIG. 1, in the micro gas sensor illustrated in FIG. 2, an electrode pad connected to the left sensing electrode 108 and an electrode pad connected to the right sensing electrode 109 are not separated but integrated with each other (referred to as LR) unlike in FIG. 1. By the electrode pad LR formed as described above, the left sensing electrode 108 and the right sensing electrode 109 are electrically connected, and a difference between electrical characteristics of the center sensing electrode 107 and the left or right sensing electrode 108 or 109 can be measured.

Next, a method of manufacturing the micro gas sensor formed as illustrated in FIGS. 1 to 3 according to the embodiments of the present invention is described in detail with reference to FIGS. 4 to 10, and main features of the micro gas sensor are described in detail.

FIGS. 4 to 10 are cross-sectional views of a device in manufacturing processes illustrated to explain the method of manufacturing the micro gas sensor according to the embodiment of the present invention. By means of the manufacturing processes, the device can be manufactured by using a silicon wafer as a base substrate and only a single pattern mask according to the present invention.

Figure 4:
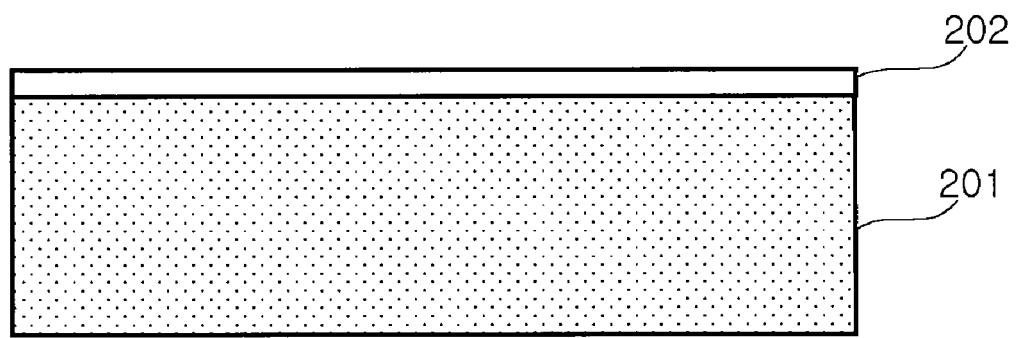
FIGS. 4 to 10 are cross-sectional views of a device in manufacturing processes illustrated to explain a method of manufacturing the micro gas sensor according to an embodiment of the present invention.

First, as illustrated in FIG. 4, an insulating layer 202 that is to be used as a masking layer to form a pattern on a silicon substrate 201 and a layer of a supporting layer (denoted by 204 in FIG. 8) is formed on an upper surface of the silicon substrate 201 with a thickness of from 0.2 μm to 5 μm. The substrate can be made of a semiconductor, a conductor, an insulator and the like.

Here, as a deposition method performed on the insulating layer 202, a low-pressure chemical vapor deposition (LPCVD), plasma enhanced chemical vapor deposition (PECVD), thermal oxidation, or the like may be used.

The insulating layer 202 may be formed as a single layer, stacked layers, or multi-layers including silicon dioxide $SiO_2$ or silicon nitride $Si_3N_4$. The insulating layer 202 has a function of insulating an electrical current flowing through a micro heater 206, a center sensing electrode 207, a left sensing electrode 208, and a right sensing electrode 209 formed in a manufacturing process in FIG. 8 from portions around the silicon substrate 201 so that the portions are not affected by the electrical current and is formed as a portion of the supporting layer 204 forming a cantilever and a bridge that is a microstructure suspended from the silicon substrate 201.

Here, in addition to the aforementioned materials, the insulating layer 202 may be formed by combining modified $SiO_2$ layers such as a borophosphosilicate glass (BPSG) layer, a phosphosilicate glass (PGS) layer, and a spin-on-glass (SOG) layer, and the like and low-stress $Si_xN_y$ layers through various thicknesses with each other.

Figure 5:
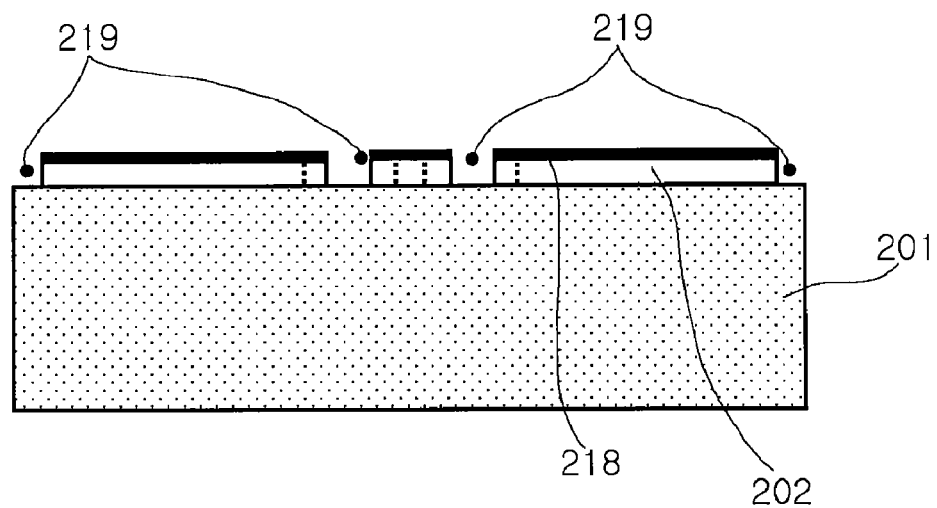

Next, as illustrated in FIG. 5, a photoresist (referred to as PR) 218 is coated on the entire upper portion of the insulating layer 202 formed as illustrated in FIG. 4 by spin-coating, and photolithography is performed by using a pattern mask to remove portions of the photoresist 218 so that the photoresist 218 is patterned by a micro line width portion 219. Here, through a single patterning process among the entire manufacturing processes, all patterns needed for the micro gas sensor according to the present invention can be formed.

Figure 7:
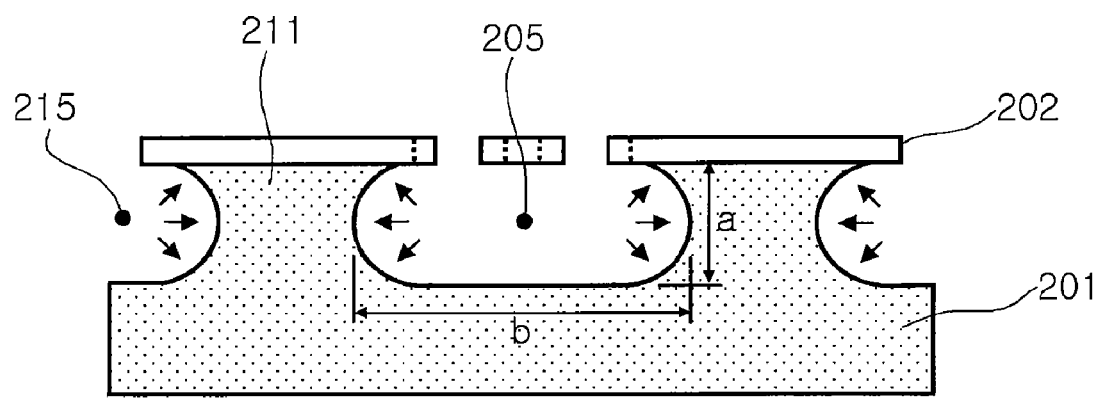
Figure 8:
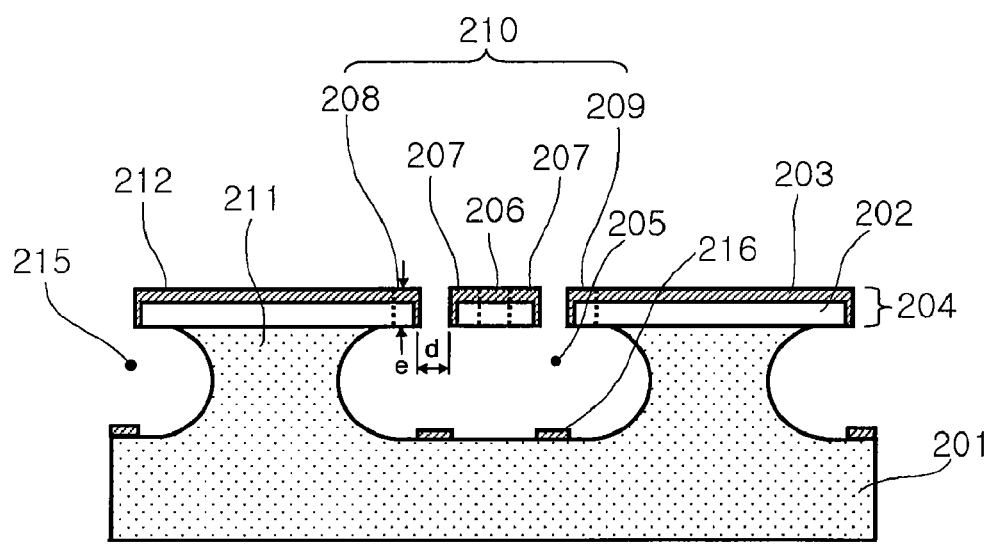

More specifically, the pattern mask includes patterns for regions where an open cavity 205 formed in a manufacturing process in FIG. 7, the electrode pad separation grooves 114 (see FIGS. 1 and 2), die separation lines 215, and the micro heater 206, the center sensing electrode 207, the left sensing electrode 208, the right sensing electrode 209, and electrode pads 212, which are formed in the manufacturing process in FIG. 8 are to be formed.

Next, by using the photoresist 218 as the masking layer for performing etching on the insulating layer 202, etching is performed on the insulating layer 202, the remaining photoresist 218 is removed, and a cleaning process is performed, thereby forming the micro line width portion 219.

Here, as an etching method of patterning the insulating layer 202, dry etching such as reactive ion etching (RIE) using plasma or charged ion particles is mainly used. In some cases, wet etching using etchant as an etching reagent may be used.

Figure 6:
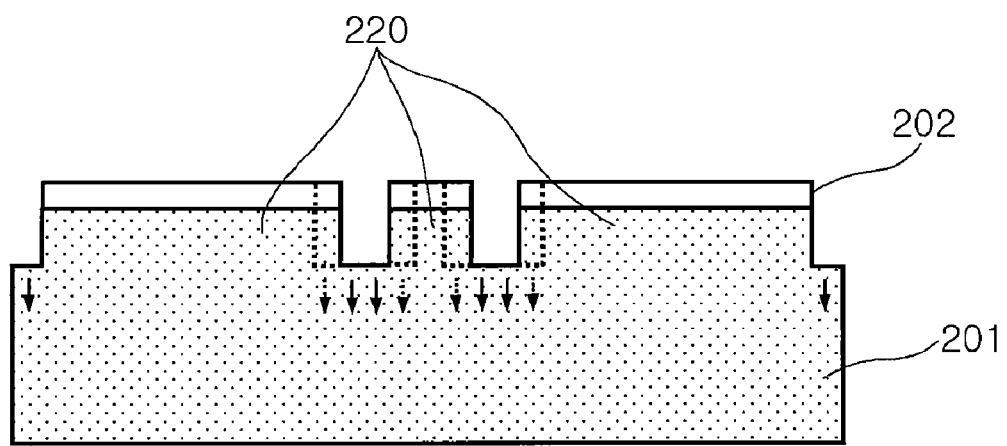

Next, as illustrated in FIG. 6, by using the insulating layer 202 as an etching masking layer, anisotropic dry etching is performed on the silicon substrate 201 in the vertical arrow direction to form a silicon trench 220 structure having a depth of from 1 μm to 500 μm from a surface of the exposed silicon substrate 201 toward a lower portion of the substrate 201.

As the dry etching, the RIE or deep-RIE for performing deep-etching in the vertical direction may be used.

Here, by controlling an etching depth of the silicon trench 220 structure, the approximate depths of the open cavity 205, the electrode pad separation groove 114 (see FIGS. 1 and 2), and the die separation line 215 which are to be formed in the manufacturing process in FIG. 7 are determined.

Next, as illustrated in FIG. 7, by using the insulating layer 202 as an etching masking layer, isotropic dry etching is performed on the silicon substrate 201 in the arrow direction to form the final regions of the open cavity 205, the electrode pad separation groove 114 (see FIGS. 1 and 2), and the die separation line 215.

The silicon trench 220 structure that is partially etched by the aforementioned process is formed by performing a sacrificial release process on the silicon to form final shapes of the open cavity 205, the electrode pad separation groove 114 (see FIGS. 1 and 2), and the die separation line 215. Simultaneously, a silicon anchor 211 is formed.

Portions of the insulating layer 202 remaining after performing the isotropic etching on the silicon substrate 201, and more particularly, portions of the insulating layer 202 micro-patterned on the open cavity 205, referring to FIGS. 1 and 2, form two cantilever array structures on the left and right, each of which has a plurality of cantilevers and suspended microstructures having a bridge having both sides with a plurality of comb-type side branches at the center. End portions of the suspended microstructures are fixed by the anchor 211.

The micro-patterned portions of the insulating layer 202 have a function of insulating the electrical current flowing through the micro heater 206, the center sensing electrode 207, the left sensing electrode 208, and the right sensing electrode 209 which are to be formed in the manufacturing process in FIG. 8 from portions around the silicon substrate 201 so that the portions are not affected by the electrical current and form a portion of the supporting layer 204 included in the final suspended microstructures.

A depth a and a width b of the open cavity 205 formed as illustrated in FIG. 7 range from 1 µm to 500 µm and from 1 µm to 10 mm, respectively. Here, the open cavity 205 is formed under the micro heater 206 that is to be formed in the manufacturing process in FIG. 8, so that heat loss to the silicon substrate 201 can be significantly reduced. As a result, even if a low voltage or a low current is applied to the micro heater 206, a gas sensing film 213 formed in a manufacturing process in FIG. 9 can be locally heated at a high temperature.

In addition, since the suspended microstructures that are not wholly fixed to the silicon substrate 201 but suspended by using the open cavity 205 are formed, thermal mass decreases, so that the gas sensing film 213 can be heated or cooled more rapidly. Here, as the width or the depth of the open cavity 205 increases as compared with a size of the micro heater 206, heat loss reduces.

As described above, the suspended microstructures are formed by performing the anisotropic and isotropic dry etchings on the silicon substrate, so that a stiction phenomenon that occurs in a manufacturing process performed between the suspended microstructures and the substrate, and is a considered as a problem in the sacrificial release process performed by wet etching in a microelectromechanical system (MEMS) can be prevented. In addition, the micro gas sensor device can be prevented from being damaged in the manufacturing processes, and a manufacturing yield can be increased.

In addition, unlike in a conventional art requiring three or more pattern masks at least to manufacture a suspended thermal insulation structure, according to the present invention, an insulation structure including the suspended microstructures having arbitrary shapes and various sizes and depths can be easily manufactured in the semiconductor manufacturing process using only a single pattern mask.

The electrode pad separation groove 114 (see FIGS. 1 and 2) that is simultaneously formed along with the suspended microstructure, has a function of electrically insulating the four (see FIG. 1) or three (see FIG. 2) electrode pads formed in the manufacturing process in FIG. 8 from each other.

Figure 9:
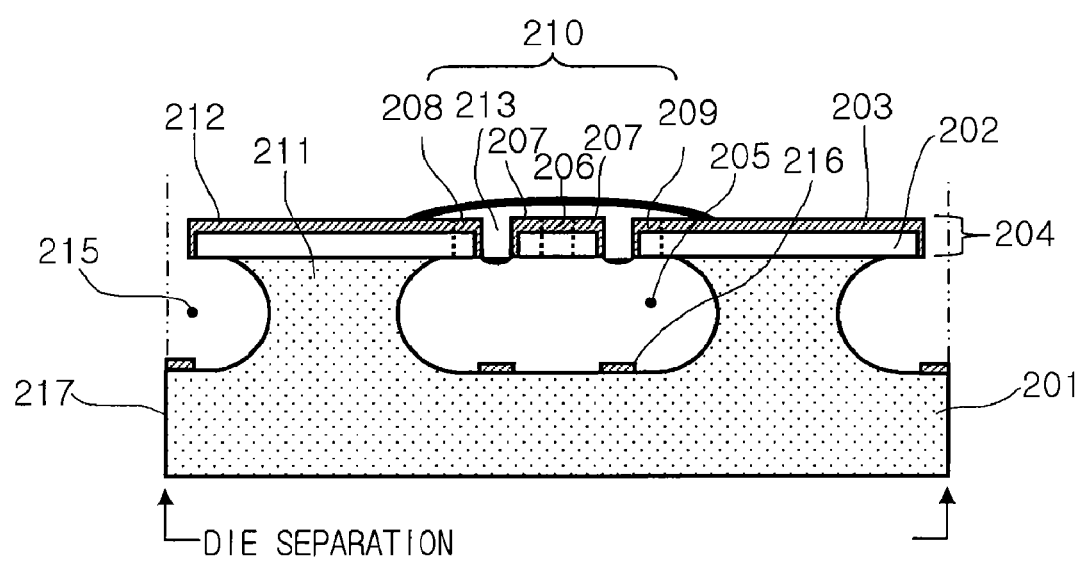

In addition, in a micro dropping process of FIG. 9, the gas sensing film 213 is accurately aligned with the center of the suspended microstructure and titrated. This requires a high-cost mechanical alignment system and results in additional cost in the manufacturing processes. Therefore, according to the present invention, the electrode pad separation groove 114 structure is applied to the device to solve the aforementioned problem technically.

Specifically, although the gas sensing film 213 is titrated and formed so as not to be accurately aligned, a liquid precursor for forming the gas sensing film 213 dropped to a portion of the electrode pad 212 that is an edge portion of the suspended microstructure (see FIGS. 1 and 2) is not contacted to the silicon substrate by surface tension and dried in a state of pending between the electrode pad separation grooves 114, so that an edge portion of the electrode pad 212 is a boundary for forming the gas sensing film 213. Therefore, the gas sensing film 213 is electrically connected only on the patterned suspended microstructure rather than on the wide electrode pad 212.

For this, a width c of the electrode pad separation groove 114 (see FIGS. 1 and 2) is generally larger than intervals d (see FIGS. 1, 2, and 8) between the center sensing electrode 207 and the left or right sensing electrode 208 or 209, which are formed by microelectrode fingers 210. According to the present invention, the width c has a value of from 10 µm to 100 µm.

In most of conventional MEMS device manufacturing processes, the sacrificial release process is performed on individual dies in a state where MEMS dies of a wafer manufactured in an intermediate state are separated from each other by a sawing machine, so that a manufacturing yield is very low, management of the die is difficult, and there is a disadvantage in terms of commercialization cost.

According to the present invention, the die separation lines 215 are simultaneously formed, so that a die 217 of the micro gas sensor is not separated in an intermediate manufacturing process and can be processed in the entire wafer level. Therefore, there are advantages in terms of commercialization, yield, and cost.

According to the present invention, in the final manufacturing process performed after the process illustrated in FIG. 9, by using the die separation lines 215 formed in advance to be partitioned according to the dies 217 on the wafer and used for device packaging, die separation (referred to as singulation) is performed so that the dies 217 of the micro gas sensor device are separated from each other on the wafer.

As illustrated in FIG. 8, a conductive layer 203 is deposited on the entire upper surface of a structure including the suspended microstructure having the open cavity 205 and the insulating layer 202, the silicon anchor 211, the electrode pad separation groove 114 (see FIGS. 1 and 2), and the die separation line 215.

Specifically, only the conductive layer 203 is deposited on the micropatterns formed in advance by using the insulating layer 202 to simultaneously form main functional units such as the micro heater 206, the center sensing electrode 207, the left sensing electrode 208, the right sensing electrode 209, and the four or three electrode pads 212, and the like on the same plane to have the same material.

When the main functional units are applied to the micro gas sensor, the units are directly contacted to the micro heater 206 for heating the gas sensing film 213 or indirectly heated at a temperature ranging from 150° C. to 500° C., so that materials for forming the main functional units must not be transformed by heat influences and have good material characteristics that can endure a high current density.

In addition, since the micro gas sensor is exposed to a severe environment such as an environment with a high temperature and humidity or toxic gas, so that a material having high oxidation resistance, environment resistance, and durability may be used for a built-up layer.

According to the present invention, a metal layer having platinum (Pt) or gold (Au) that can be easily implemented in the semiconductor manufacturing process, show stable operation characteristics, and have excellent thermal resistance and physical and chemical characteristics as a base material may be used as the conductive layer 203.

Returning to FIG. 8, in order to deposit the metal layer as the conductive layer 203, sputtering or e-beam evaporation is first performed to promote adhesion and crystal orientation between the metal layer and the insulating layer 202 and have a function of preventing the material of the conductive layer from diffusion, a titanium (Ti) layer, a titanium tungsten (TiW) layer, or a chromium (Cr) layer with a small thickness is deposited as a lower basal layer, and then a Pt thin film or an Au thin film having a thickness of from 0.1 μm to 5 μm is deposited thereon to form a stacked metal layer such as a Ti/Pt layer, a TiW/Pt layer, a Cr/Pt layer, a Ti/Au layer, a TiW/Au layer, or a Cr/Au layer.

Here, the lower basal layer may be combined with electrical conductive layers having metals such as TiN, $TiO_2$, Ta, TaN, Ti/TiN, Ti/Ni, Ti/TiW, Ti/Pt, and the like as bases.

Therefore, electrical insulation and separation can be automatically implemented just by depositing the conductive layer on the micropatterns including the open cavity 205, the silicon anchor 211, the electrode pad separation groove 114, and the die separation line 215 formed in advance.

Here, a conductive layer 216 is formed at a lower portion of the silicon substrate 201 where the open cavity 205, the electrode pad separation groove 114, and the die separation line 215 are formed. However, the conductive layer 216 is electrically insulated from the suspended structure by the insulating layer and the silicon anchor 211. Therefore, additional metal layer patterning processes such as a general lift-off process are not needed.

As a result, a thickness of the supporting layer 204 having the suspended microstructure including the insulating layer 202 and the conductive layer 203 ranges from 0.3 μm to 10 μm.

When the suspended structure of the micro gas sensor is repeatedly heated or cooled by the micro heater 206, thermal stress occurs due to lack of temperature uniformity, and influences may occur due to external mechanical impacts.

The built-up layer formed by combining the insulating layer 202 with the metal layer 203 and used as the supporting layer 204 has a higher elastic coefficient and thermal conductivity as compared with a conventional basal built-up layer which has been used for the micro sensor and has a structure of a single layer including a $SiO_2$ layer or the $Si_3N_4$ layer having brittleness and a low thermal conductivity, a stacked structure including the layers, or a multi-layer structure including the layers. Here, as the elastic coefficient is increased, a structural and mechanical restoring force is increased. In addition, as the thermal conductivity is increased, the lack of temperature uniformity in a thin film is reduced, and the thermal stress is decreased. Therefore, the supporting layer 204 according to the present invention has a function of providing durability so that the micro gas sensor can resist thermal and mechanical impacts.

The micro heater 206 that is formed by depositing the metal layer, that is, the conductive layer 203 according to the present invention has low power consumption, a short response time, and stable operation characteristics. Particularly, the micro heater 206 is designed to have a resistance of from several to tens of ohms.

The micro heater 206 disposed at the center portion of the micro gas sensor device is formed on the open cavity 205 and has a suspended bridge microstructure with a relatively large width on the silicon substrate 201. At both sides of the bridge structure, microelectrode fingers 210 are attached in cantilever arrays to have a shape of a comb or a fish bone.

Here, the microelectrode fingers 210 attached to the both sides of the micro heater 206 serve as a heat spreader for conducting heat generated at the center portion of the micro heater 206 to the both side portions when the gas sensing film 213 (see FIG. 9) is heated by the micro heater 206 so that the temperature of the gas sensing film 213 is uniform.

The shape of the micro heater 206 is not limited to a specific shape such as the bridge structure. The micro heater 206 is stably connected to external electrical wires and applied with power without electrical loss through the two electrode pads 212 (denoted by H and G in FIGS. 1 and 2) formed on the same plane as the micro heater 206 by depositing the metal layer.

In order for the micro heater 206 to heat the gas sensing film 213 (see FIG. 9) and sense changes in electrical characteristics of the gas sensing film 213 according to changes in the concentration of an interesting gas existing around the micro has sensor device, a sensing electrode that is contacted to the gas sensing film 213 is needed.

For this, according to the present invention, the three sensing electrodes, that is, the center sensing electrode 207, and the left and right sensing electrodes 208 and 209 that are counterparts to the center sensing electrode 207 are provided. The left and right sensing electrodes 208 and 209 may be integrated as a single sensing electrode (see FIG. 2). By using an external circuit, a difference between electrical characteristics of the center sensing electrode 207 and the left sensing electrode 208 or the right sensing electrode 209 that is the counterpart to the center sensing electrode 207 is measured to quantitate the electrical conductivity of the gas sensing film 213 and measure the concentrate of the interesting gas.

Otherwise, as illustrated in FIG. 2, the left and right sensing electrodes 208 and 209 may be electrically connected to each other and a voltage difference between the center sensing electrode 207 and the connected electrode may be measured.

Here, three or two electrode pads 212 (denoted by G, L, and R in FIG. 1 or G and LR in FIG. 2) connected to the corresponding sensing electrodes for connection to external electrical wires are included.

The micro heater 206 formed to be suspended for electrical insulation and thermal insulation from the substrate 201 manufactured as described above and the microelectrode fingers 210 attached to the micro heater 206 have another function of forming the center sensing electrode 207 having the shape of the comb, that is, the fish bone.

Specifically, one or more microelectrode fingers 210 are branched from the both side portions of the suspended thick bridge structure in the cantilever array, and this forms a side electrode for forming a pair of IDE sensing electrodes that are insulated from each other.

The left and right sensing electrodes 208 and 209 that face each other. Each of the left and right sensing electrodes 208 and 209 has the cantilever array including the one or more branched microelectrode fingers 210. In addition, each of the left and right sensing electrodes 208 and 209 has an end portion for forming an IDE electrode that faces the center sensing electrode 207 at the center portion of the micro gas sensor and the other end portion connected to the two (see FIG. 1) or one (see FIG. 2) electrode pads 212 for stable connection to the external electrical wires.

According to the present invention, intervals d (referred to as microelectrode finger spacing) between the three sensing electrodes 207, 208, and 209 in the cantilever array having the microelectrode fingers 210 are equal and range from 0.1 μm to 10 μm.

Specifically, a pair of IDE electrodes that are finally formed include the microelectrode fingers 210 of the three sensing electrodes 207, 208, and 209 that are suspended to be disposed at the center portion of the sensor device and are automatically and electrically insulated from each other. According to the present invention, a shape of each of the sensing electrodes 207, 208, and 209 is a square but not limited to a specific shape.

As described above, in the semiconductor manufacturing processes using a single pattern mask as illustrated in FIGS. 4 to 8, all functional units excluding the gas sensing film among the components of the micro gas sensor device can be successfully manufactured.

Next, as illustrated in FIG. 9, a process for forming the gas sensing film 213 that reacts to a gas to measure the concentrate of the gas on the center portion of the suspended structure as the last material is performed.

A liquid precursor for the gas sensing film is prepared by mixing materials including metal oxide, metal, semiconductors, or polymer or nano-materials such as nano-particles, nano-wires, nano-tubes, and the like with a solvent or a solvent with a binder to have a proper concentration.

Next, the liquid precursor is dropped to a portion forming the pair of IDE electrodes of the micro-patterned suspended structure at the center portion of a front surface of the substrate with a volume of several to tens of hundreds of nano-liters by micro dropping once or several times.

At the center portion of the micro gas sensor device to which the liquid precursor is dropped, the microelectrode finger spacings d formed at the pair of IDE electrodes including the microelectrode fingers 210 in the cantilever arrays of the three sensing electrodes 207, 208, and 209 range from 0.1 µm to 10 µm, and a thickness e of the supporting layer 204 ranges from 0.3 µm to 10 µm.

The liquid precursor dropped on the micro patterns penetrates between the microelectrode finger spacings by capillary force in a direction of a depth of the supporting layer and is hung down from the lower portion of the insulating layer by surface tension, so that the liquid precursor is not contacted to the silicon substrate 201 by the open cavity 205 that is deep.

In addition, a liquid phase component of the liquid precursor is dried slowly at the room temperature and automatically levels in horizontal, so that only a solid phase component of the liquid precursor fills and remains between the microelectrode finger spacings.

Thereafter, when the liquid precursor is additionally dried or a post-annealing process is performed thereon, remaining solvent or binder is volatilized, and only the gas sensing film 213 is formed on the top surface of the sensor device in a solid state with a diameter of tens to hundreds µm.

Here, the precursor for forming the gas sensing film 213 dropped to a portion excluding the micro structure suspended by the electrode pad separation groove 114 (see FIGS. 1 and 2) formed by performing dry etching on the silicon substrate 201 in advance to have a shape of X in the manufacturing process in FIG. 7, dries and does not contact the lower portion of the silicon substrate 201 by the surface tension, and a boundary of the dropped precursor is formed throughout edges of the electrode pad 212.

Only the gas sensing film 213 that is finally formed on the suspended microstructure is electrically connected to the microelectrode fingers 210 of the center sensing electrode 207, the left sensing electrode 208, and the right sensing electrode 209. Therefore, when the gas sensing film 213 is formed by the micro dropping, a micro mechanical alignment process to form the gas sensing film 213 is not needed. In addition, the shape of the electrode pad separation groove 114 is not limited to a specific shape such as the shape of X.

As described above, the gas sensing film 213 is formed to fill the microelectrode finger spacings formed between the microelectrode fingers 210 having depths ranging from 0.3 µm to 10 µm in the vertical direction. Therefore, the total surface area of the gas sensing film 213 that directly contacts the center sensing electrode 207, the left sensing electrode 208, and the right sensing electrode 209 is significantly increased. Therefore, an output of the micro gas sensor device corresponding to changes in the concentration of the interesting, that is, a sensitivity of the sensor can be improved.

In addition, the gas sensing film 213 that is made of various types of materials such as metal oxide, metal, semiconductors, polymer, nano-materials, and the like can be directly formed only around the sensing electrodes 207, 208, and 209 by using the principle of the capillary force and the surface tension of the liquid without additional processes such as micro-patterning. The gas sensing film can be formed by a micro dropping method, an e-beam evaporation method, a sputtering method, a pulsed laser deposition method, a sol-gel method, a chemical vapor deposition (CVD) method, a spray coating method, a dip coating method, or a screen printing method.

In a case where nano-wires are used for the gas sensing film 213, for example, if the nano-materials are microstructurally arrayed so as to be properly hung down from the both ends of the sensing electrodes 207, 208, and 209, the gas sensing characteristics can be further improved. For this, when the micro dropping is performed in a state where a direct current (DC) or an alternating current (AC) bias voltage is applied to the both ends of the pair of the IDE electrodes including the center sensing electrode 207 and the left sensing electrode 208 or the right sensing electrode 209, due to a voltage difference between the IDE electrodes, the nano-wires are microstructurally aligned to be hung down from the both ends of the IDE electrodes.

Here, although it is exemplified that the micro dropping is used to form the gas sensing film 213, a method of forming the gas sensing film 213 is not limited to the micro dropping. For example, after a shadow mask that is manufactured in advance by using e-beam evaporation, sputtering, pulsed laser deposition, or the like is deposited on the substrate 201 wafer, the gas sensing film 213 may be deposited. In addition, sol-gel, chemical vapor deposition (CVD), spray coating, dip coating, screen printing, or the like may be used to form the gas sensing film 213. In addition, a range of a thickness of the gas sensing film may be extended according to a desired range of sensitivity of the micro gas sensor device.

For example, when the micro gas sensor device is mounted on a vacuum furnace and a bias voltage is applied to the both end portions of the micro heater 206 of the sensor device while flowing materials for depositing the nano-material, due to a heat insulation structure formed by the open cavity 205 and the suspended microstructure, a deposition reaction of the nano-materials proceeds first around the center sensing electrode 207 that is heated at a high temperature, and the reactant grows as time elapses so as to be connected to the left sensing electrode 208 and the right sensing electrode 209. Therefore, without the micro patterning, the nano-materials can be formed only around the sensing electrodes 207, 208, and 209 as the gas sensing film 213 in-situ.

Here, a material for the gas sensing film 213 is not limited to a specific material, and any thin film material showing changes in electrical characteristics according to a gas concentration can be used. Specifically, the material selected from the group consisting of metal oxide, metal, semiconductors, polymer, and nano-materials or a combination thereof may be used.

When the gas sensing film 213 that is finally obtained to have a desired thickness is the metal oxide, the gas sensing film 213 is post-annealed in an environment including oxygen (such as $O_2$, $O_3$, $N_2O$, and the like) or in the air at a temperature of from 300° C. to 600° C. for a long time to improve film quality and stabilization of the thin film.

To perform packaging and assembly processes such as a die attachment process or a wire bonding process on a package by using an adhesive or a solder, the micro gas sensor devices that are formed on the entire substrate 201 wafer and each of which includes the gas sensing film 213 in the continuous processes are partitioned and separated from each other by the dies 217.

Specifically, in the manufacturing process in FIG. 9, by using the die separation lines 215 formed to partition the wafer according to the dies 217, the dies 217 of the micro gas sensor device on the substrate wafer are separated from each other. Thereafter, the separated dies 217 are attached to the package (not shown in the figure) by using an adhesive or a solder.

Figure 10:
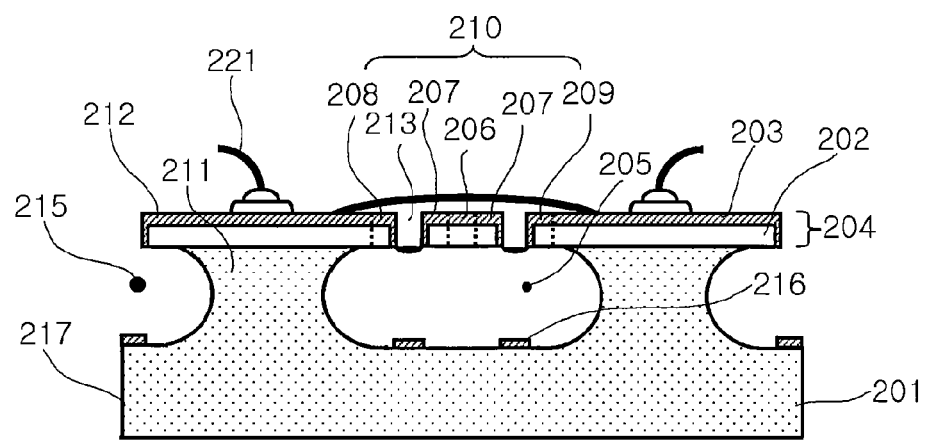

Last, FIG. 10 schematically illustrates a state of each separated die of the micro gas sensor device in which wire bonding 221 for connecting metal wires to the four or three electrode pads 212 formed to connect the micro heater 206, the center sensing electrode 207, the left sensing electrode 208, and the right sensing electrode 209 to the external electrical wires is finished. Intermediate packaging and assembly processes for this are well known, so that a detailed description thereof is omitted.

In order to measure the gas concentration, first, a predetermined power is applied to the both end portions of the two electrode pads 212 (denoted by H and G in FIGS. 1 and 2) serving as the micro heater 206 to locally heat the gas sensing film 213 at the center portion of the sensor at a predetermined temperature.

In this state, a change in characteristics of the gas sensing film 213 that occurs when existing gas is absorbed into or desorbed from the gas sensing film 213 according to the concentration can be simply determined by measuring a difference in electrical characteristics between the left or right electrode pads 212 and the grounding electrode pad 112 (denoted by L, R, G in FIG. 1, respectively, or denoted by LR and G in FIG. 2, respectively) connected with external circuit and quantitating an electrical conductivity of the gas sensing film 113.

In addition, for more accurate measurement, after recovering the gas sensing film 213 to an initial state by compulsively heating gas and moisture absorbed into the gas sensing film 213 in advance by using the micro heater 206 so that the gas and moisture are removed, the concentration of the interesting gas is measured.

Figure 11A:
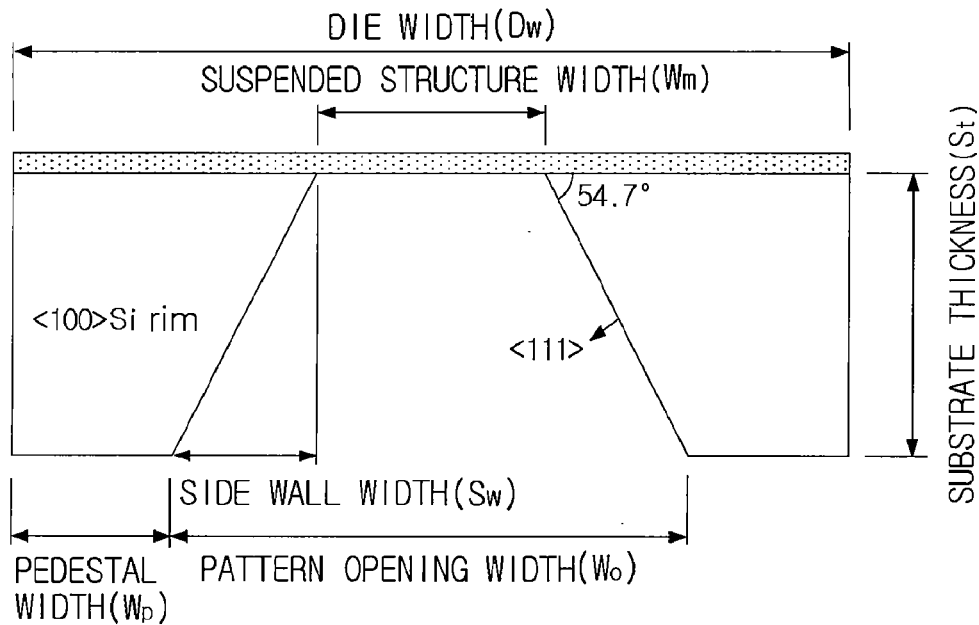
FIGS. 11A and 11B are a schematic cross-sectional view for comparing die sizes of a bulk-micromachined type micro gas sensor device formed by conventional wet silicon etching with the micro gas sensor device according to the embodiment of the present invention.
Figure 11B:
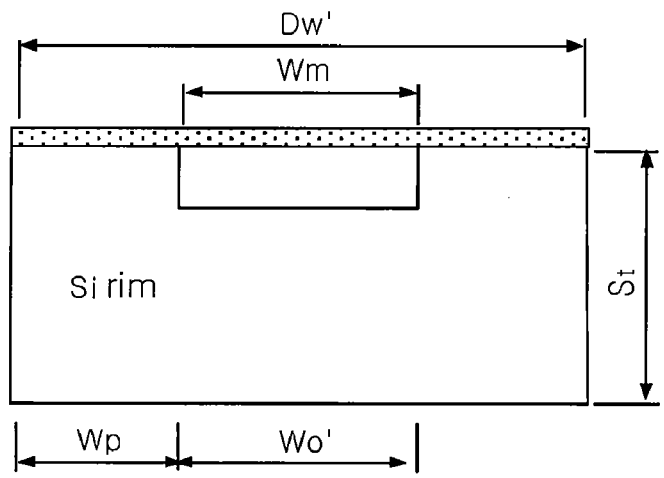

FIGS. 11a and 11b are schematic cross-sectional views for comparing die sizes of a micro gas sensor device formed by etching a silicon rear surface in a conventional wet etching and the micro gas sensor device according to the embodiment of the present invention.

The micro gas sensor device having a shape formed by performing the conventional wet silicon etching as illustrated in the cross-sectional view of FIG. 11A includes the suspended structure having a width of $W_m$ by using the insulating layer deposited on the front surface of the substrate and by performing anisotropic etching with a wet silicon etchant such as potassium hydroxide (KOH), tetramethylammonium hydroxide (TMAH), ethylenediamine pyrocatechol (EDP), and the like through a square pattern opening width $W_o$ formed at the rear surface of the silicon substrate having a commonly used <100> crystallization direction to a silicon substrate thickness $S_t$. Here, the pattern opening width $W_o$ at the substrate rear surface has to satisfy geometric factors of Equation 1, and a die width $D_w$ of the device is determined by Equation 2.

$$W_o \geq W_m + \sqrt{2} S_t \quad \text{[Equation 1]}$$

$$D_w = W_o + 2W_p \quad \text{[Equation 2]}$$

Therefore, the die width $D_w$ of the micro gas sensor device formed in the aforementioned process has to be designed to be large enough in consideration of a side wall width $S_w$, and this is related to the substrate thickness $S_t$, the pattern opening width $W_o$, and a pedestal width $W_p$ that is a lower width of a silicon rim.

In addition, an open cavity that is formed at an angle of 54.7° to an etch front in a <111> crystallization direction are simultaneously manufactured along with a final suspended structure (membranes, bridges, cantilevers, and the like), and the shape of the suspended structure is generally a rectangular shape. When the shape is not the rectangular shape, there is a problem of etching compensation for corner portions in the manufacturing processes.

When the aforementioned structure is compared with the schematic cross-sectional view illustrating the die of the micro gas sensor device according to the embodiment of the present invention, according to the present invention, dry etching is performed on the silicon at the front surface to form the suspended structure, so that there is an advantage in that the suspended structure having an arbitrary shape can be manufactured without influences due to the pedestal width $W_p$ and the substrate thickness $S_t$ due to the crystallization direction of the silicon.

Therefore, geometric numerical values of the micro gas sensor die have relationships as represented by Equations 3 and 4.

$$W_o' \sim W_m \quad \text{[Equation 3]}$$

$$D_w' = W_o' + 2W_p \quad \text{[Equation 4]}$$

Here, $W_o'$ and $D_w'$ denote a pattern opening width and a die width of the device seen and projected from the substrate rear surface, respectively.

Therefore, according to the present invention, when the same cavity size is guaranteed, as a size of the device die decreases, the total number of dies that can be obtained from a given wafer diameter is increased. Therefore, advantages of decrease in package size and quality improvement due to reduction in a defect density and drifts in the manufacturing processes can be achieved. In addition, since the total package size is reduced, device manufacturing cost can be significantly reduced.

For example, when it is assumed that the silicon substrate thickness, the suspended structure width, and the pedestal width are 400 μm, 1,500 μm, and 300 μm, respectively, the die width in FIG. 11B according to the present invention is about 2,100 μm, so that the die width is decreased by about 21% as compared with a case in FIG. 11A. In addition, when an area of the die is square, the device size can be reduced by about 38%.

As described above, the micro gas sensor proposed according to the present invention, is manufactured by using silicon dry etching techniques generally formed on the substrate front surface but not the conventional wet silicon etching performed on the substrate rear surface. Therefore, an arbitrary suspended structure can be mass-produced with a miniature size, high precision, and low cost.

Figure 12:
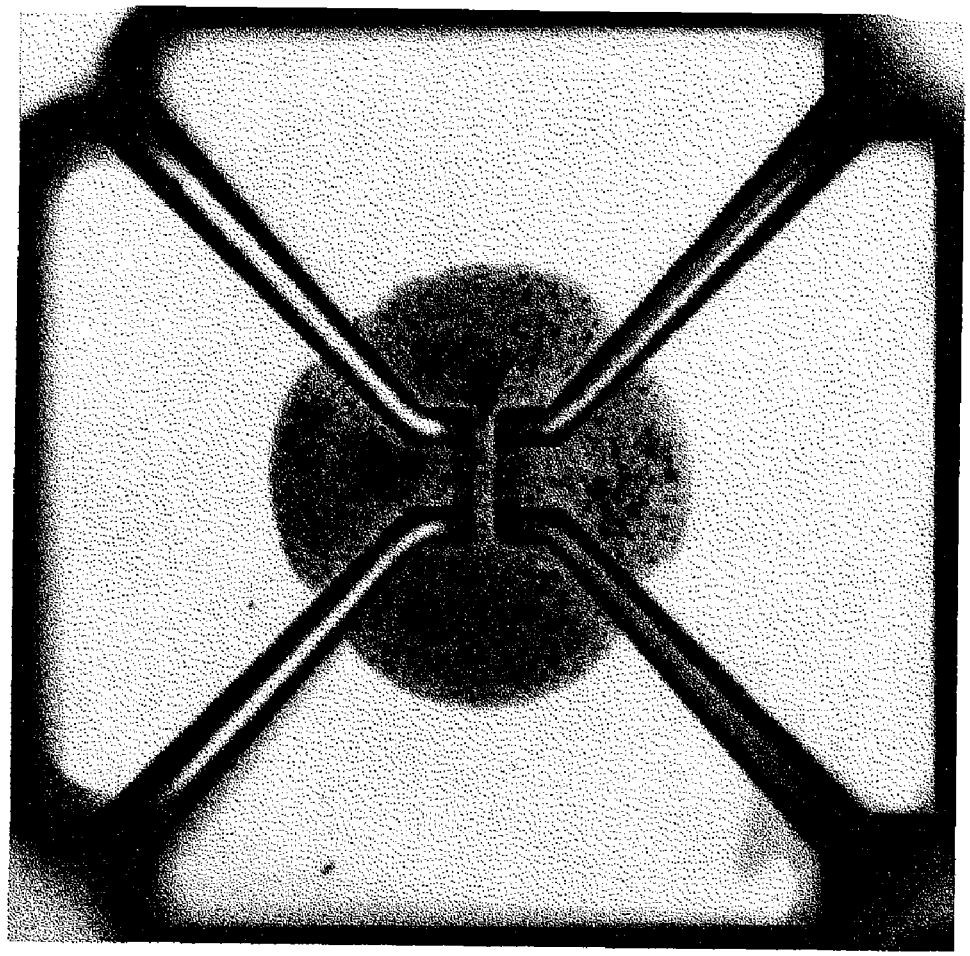
FIG. 12 is a picture showing a top plan view structure of the micro gas sensor device manufactured according to the present invention.

In addition, FIG. 12 illustrates that, for the micro gas sensor device having a size of 1.2×1.2 mm² manufactured in the aforementioned processes according to the present invention, the open cavity formed at the lower portion of the silicon substrate, the electrode pad separation groove, the die separation line, the silicon anchor, the supporting layer including the SiO₂ insulating layer and the Ti/Pt conductive layer formed thereon, the micro heater having the bridge structure made of Ti/Pt, the center sensing electrode having the shape of comb, the left and right sensing electrodes having a number of microelectrode fingers, the four electrode pads, and the $SnO_2$-based gas sensing film formed at the top layer, are properly formed on the suspended microstructure.

According to the present invention, the sensor has low power consumption, a rapid heating and cooling time, high durability, and high sensitivity characteristics, and the gas sensing film can be easily formed by using various materials. In addition, only a single patterning process using a single pattern mask is used in the semiconductor manufacturing processes, so that the micro gas sensor can be miniaturized and mass-produced at low cost.

In addition, according to the present invention, the suspended structure can be formed by anisotropic and isotropic dry etching on the silicon substrate, so that a stiction phenomenon that may occur in a process performed between the suspended structure and the substrate can be prevented, and manufacturing yield can be increased. In addition, the die separation line is simultaneously formed in the etching process for forming the pattern, so that the dies are not separated in the intermediate manufacturing process but are separated in the device packaging process, so that there are advantages in terms of the manufacturing yield and low cost.

While the present invention has been shown and described in connection with the exemplary embodiments, it will be apparent to those skilled in the art that modifications and variations can be made without departing from the spirit and scope of the invention as defined by the appended claims.

What is claimed is:

1. A micro gas sensor comprising:
   a substrate;
   an open cavity formed in the substrate;
   an electrode pad separation grooves formed on the substrate;
   a first and a second electrode pads formed over the substrate and electrically insulated from each other by the electrode pad separation grooves;
   a micro heater connected to the first electrode pad and having a bridge structure suspended over the open cavity and a bottom surface that is directly in contact with the open cavity;
   a first sensing electrode extending from the first electrode pad and suspended over the open cavity;
   a second sensing electrode extending from the second electrode pad and suspended over the open cavity, wherein the second electrode is electrically insulated from the first sensing electrode by a gap present between the first and the second sensing electrodes; and
   a gas sensing film electrically coupled to the micro heater and filling the gap between the first and the second sensing electrodes.

2. The micro gas sensor of claim 1, further comprising die separation lines formed on the substrate for separating the micro gas sensor from another micro gas sensor.

3. The micro gas sensor of claim 1, wherein the substrate is made of a material selected from the group consisting of semiconductor, conductor, and insulator.

4. The micro gas sensor of claim 1, wherein the electrode pad separation groove has a shape of X so that the gas sensing film is not contacted to the lower portion of the substrate and is hung down between the first and the second electrode pads.

5. The micro gas sensor of claim 1, wherein each of the micro heater, the first and the second sensing electrodes, and the first and the second electrode pads is formed of a stack structure including an insulating layer and a conductive layer.

6. The micro gas sensor of claim 5, wherein the insulating layer includes any of a silicon oxide ($SiO_2$) layer, a silicon nitride ($Si_3N_4$) layer, and a modified silicon oxide layer,
   wherein the modified silicon oxide layer includes any of a borophosphosilicate glass (BPSG) layer, a phosphosilicate glass (PSG) layer, and a spin-an-glass (SOG) layer.

7. The micro gas sensor of claim 5, wherein the conductive layer is made of one or more of metal and a material including metal.

8. The micro gas sensor of claim 5, wherein the conductive layer has a high thermal conductivity.

9. The micro gas sensor of claim 1, wherein the first electrode pads is electrically connected to the micro heater.

10. The micro gas sensor of claim 1, wherein the first sensing electrode includes a center sensing electrode, and
    wherein the second sensing electrode includes a left sensing electrode, and a right sensing electrode which have a suspended structure for sensing changes in electrical characteristics according to reaction of the gas sensing film.

11. The micro gas sensor of claim 10, wherein each of the center sensing electrode, the left sensing electrode, and the right sensing electrode include a plurality of microelectrode fingers in suspended cantilever shape.

12. The micro gas sensor of claim 10, wherein the center sensing electrode is connected to the micro heater and has a structure in a shape of a comb or a fish bone.

13. The micro gas sensor of claim 10, wherein one end portion of each of the left sensing electrode and the right sensing electrode faces the center sensing electrode to form a pair of IDEs (interdigitated electrodes) that are electrically insulated from each other, and the other end portion of each of the left sensing electrode and the right sensing electrode is connected to the second electrode pad so as to be connected to an external electrical wire.

14. The micro gas sensor of claim 10, wherein the left sensing electrode and the right sensing electrode are electrically connected to a plurality of the electrode pads to form a single sensing electrode.

15. The micro gas sensor of claim 10, wherein the gas sensing film is buried or hung down between microelectrode finger spacings of a plurality of the sensing electrodes composed of the center sensing electrode, the left sensing electrode, and the right sensing electrode.

16. The micro gas sensor of claim 15, wherein the gas sensing film is formed one of materials including metal oxide, metal, semiconductor, polymer, and nano-materials or a combination thereof.

17. A method of manufacturing a micro gas sensor comprising:
    forming an insulating layer on a substrate;
    forming a photoresist over the insulating layer and performing a patterning process onto the insulating layer by using a pattern mask to obtain a patterned insulating layer;
    forming a first and a second silicon trenches in the substrate in a predetermined depth by performing a first etching process using the patterned insulating layer as an etching masking layer;
    performing a second etching process on the substrate including the first and the second trenches to form an open cavity interconnecting lower surfaces of the first and the second trenches while maintaining the patterned insulating layer suspended over the open cavity, thereby forming a first insulating layer suspended over the open cavity and a second insulating layer formed over the substrate, wherein the first and the second insulating layers are separated from each other by the open cavity;

forming a conductive layer over the first and the second insulating layers to obtain a first electrode pad formed over the first insulating layer, a second electrode pad formed over the second insulating layer, a micro heater formed over the first insulating layer and electronically coupled to the first electrode pad, a first sensing electrode extending from the first electrode pad, and a second sensing electrode extending from the second electrode pad, wherein the first and the second sensing electrodes are suspended over the open cavity and insulated from each other by a gap formed between the first and the second sensing electrodes wherein the micro heater has a bottom surface that is directly in contact with the open cavity; and forming a gas sensing film filling the gap between the first and the second sensing electrodes.

18. The method of claim 17, further comprising forming die separation lines separating the first electrode pad from the second electrode pad.

19. The method of claim 17, wherein the first etching process is performed by anisotropic dry etching on the substrate by using a reactive ion etching (RIE) process or a deep-RIE process.

20. The method of claim 17, wherein the second etching process is isotropic dry etching.

21. The method of claim 17, wherein the micro heater has a bridge structure and is integrated with the first electrode pad.

22. The method of claim 17, wherein the first sensing electrodes includes a center sensing electrode in a comb-shape and electrically connected to the micro heater, and
wherein the second sensing electrode includes a left sensing electrode and a right sensing electrode each of which interdigitates with the center sensing electrode with a gap.

23. The method of claim 17, wherein the gas sensing film is formed using a liquid precursor including any of metal oxide, metal, semiconductors, polymer, nano-materials and a combination thereof.

24. The method of claim 23, wherein in the step of forming the gas sensing film, comprising:
dropping the liquid precursor over the gap between the first and the second sensing electrodes under such a condition that the liquid precursor flows into the gap between the first and the second sensing electrodes by a capillary force and hangs up in the gap substantially without being drop down to the bottom of the open cavity by surface tension.

25. The method of claim 17, wherein the step of forming the gas sensing film is performed by micro dropping, e-beam evaporation, sputtering, pulsed laser deposition, sol-gel, chemical vapor deposition (CVD), spray coating, dip coating, or screen printing.

* * * * *